(12) United States Patent
Banerjee et al.

(10) Patent No.: US 9,597,396 B2
(45) Date of Patent: *Mar. 21, 2017

(54) FORMOTEROL/STEROID BRONCHODILATING COMPOSITIONS AND METHODS OF USE THEREOF

(71) Applicant: Mylan Specialty L.P., Basking Ridge, NJ (US)

(72) Inventors: Partha S. Banerjee, Wynnewood, CA (US); Imtiaz Chaudry, American Canyon, CA (US); Stephen Pham, Sacramento, CA (US)

(73) Assignee: Mylan Specialty LP NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/142,178

(22) Filed: Dec. 27, 2013

(65) Prior Publication Data

US 2014/0171398 A1    Jun. 19, 2014

Related U.S. Application Data

(60) Continuation of application No. 12/625,328, filed on Nov. 24, 2009, now Pat. No. 8,623,851, which is a continuation of application No. 10/145,978, filed on May 13, 2002, now abandoned, which is a division of application No. 09/887,496, filed on Jun. 22, 2001, now abandoned.

(60) Provisional application No. 60/284,607, filed on Apr. 17, 2001.

(51) Int. Cl.

| A61K 31/58 | (2006.01) |
|---|---|
| A61K 31/135 | (2006.01) |
| A61K 9/00 | (2006.01) |
| A61K 47/10 | (2017.01) |
| A61K 31/167 | (2006.01) |
| A61K 31/537 | (2006.01) |
| A61K 31/56 | (2006.01) |
| A61K 31/573 | (2006.01) |
| A61K 45/06 | (2006.01) |
| A61K 31/191 | (2006.01) |
| A61K 31/568 | (2006.01) |
| A61K 47/02 | (2006.01) |

(52) U.S. Cl.
CPC ........... *A61K 47/10* (2013.01); *A61K 9/0078* (2013.01); *A61K 31/167* (2013.01); *A61K 31/191* (2013.01); *A61K 31/537* (2013.01); *A61K 31/56* (2013.01); *A61K 31/568* (2013.01); *A61K 31/573* (2013.01); *A61K 31/58* (2013.01); *A61K 45/06* (2013.01); *A61K 47/02* (2013.01)

(58) Field of Classification Search
CPC .............................. C07J 3/005; A61K 31/167
USPC ................................................ 514/173, 653
See application file for complete search history.

(56) References Cited

U.S. PATENT DOCUMENTS

| 3,929,768 A | 12/1975 | Brattsand et al. |
|---|---|---|
| 3,994,974 A | 11/1976 | Murakami et al. |
| 4,335,121 A | 6/1982 | Phillipps et al. |
| 4,992,474 A | 2/1991 | Skidmore et al. |
| 5,033,252 A | 7/1991 | Carter |
| 5,052,558 A | 10/1991 | Carter |
| 5,126,375 A | 6/1992 | Skidmore et al. |
| 5,225,445 A | 7/1993 | Skidmore et al. |
| 5,270,305 A | 12/1993 | Palmer |
| 5,275,212 A | 1/1994 | Moris |
| 5,290,815 A | 3/1994 | Johnson et al. |
| 5,323,907 A | 6/1994 | Kalvelage |
| 5,525,623 A | 6/1996 | Spear et al. |
| 5,602,110 A | 2/1997 | Drumm et al. |
| 5,654,276 A | 8/1997 | Barrett et al. |
| 5,668,110 A | 9/1997 | Barrett et al. |
| 5,674,860 A | 10/1997 | Carling et al. |
| 5,677,280 A | 10/1997 | Barrett et al. |
| 5,677,809 A | 10/1997 | Kadlec |
| 5,683,983 A | 11/1997 | Barrett et al. |
| 5,691,336 A | 11/1997 | Dorn et al. |
| 5,733,526 A | 3/1998 | Trevino et al. |
| 5,750,549 A | 5/1998 | Caldwell et al. |
| 5,780,467 A | 7/1998 | Dorn et al. |
| 5,795,564 A | 8/1998 | Aberg et al. |
| 5,874,063 A | 2/1999 | Briggner et al. |
| 5,874,481 A | 2/1999 | Weers et al. |
| 5,877,191 A | 3/1999 | Caldwell et al. |
| 5,929,094 A | 7/1999 | Durette et al. |
| 5,965,622 A | 10/1999 | Senanayake |
| 5,972,919 A | 10/1999 | Carling et al. |
| 5,980,949 A | 11/1999 | Trofast |

(Continued)

FOREIGN PATENT DOCUMENTS

| DE | 2305092 A1 | 8/1973 |
|---|---|---|
| DE | 19541689 A1 | 5/1996 |

(Continued)

OTHER PUBLICATIONS

Dey v. Sepracor: 1:07-cv-2353; Complaint.
Dey v. Sepracor: 1:07-cv-2353; Answer and Counterclaims.
Dey v. Sepracor: 1:07-cv-2353; Reply to Counterclaims.
Dey v. Sepracor: 1:07-cv-2353; Answer to Additional Claims.
Dey v. Sepracor: 1:07-cv-2353; Discovery Plan.
Lachman et al., "Chapter 26: Kinetic Principles and Stability Testing", The Theory and Practice of Industrial Pharmacy, 1986, 3rd Edition.
Whelan et al., "Comparison of the Anti-Inflammatory Properties of Formoterol, Salbutamol, and Salmeterol in Guinea-Pig Skin and Lung", British Journal of Pharmacology, 1993, pp. 613-618, 110.

(Continued)

*Primary Examiner* — Shengjun Wang

(57) ABSTRACT

Bronchodilating compositions and methods are provided. The compositions are intended for administration as a nebulized aerosol. In certain embodiments, the compositions contain formoterol, or a derivative thereof, and a steroidal anti-inflammatory agent. Methods for treatment, prevention, or amelioration of one or more symptoms of bronchoconstrictive disorders using the compositions provided herein are also provided.

20 Claims, No Drawings

(56) References Cited

U.S. PATENT DOCUMENTS

| | | |
|---|---|---|
| 5,983,956 A | 11/1999 | Trofast |
| 6,004,537 A | 12/1999 | Blondino et al. |
| 6,030,604 A | 2/2000 | Trofast |
| 6,040,344 A | 3/2000 | Gao et al. |
| 6,041,777 A | 3/2000 | Faithfull et al. |
| 6,068,833 A | 5/2000 | Aberg et al. |
| 6,071,971 A | 6/2000 | Senanayake |
| 6,126,919 A | 10/2000 | Stefely et al. |
| 6,136,603 A | 10/2000 | Dean et al. |
| 6,150,418 A | 11/2000 | Hochrainer et al. |
| 6,161,536 A | 12/2000 | Redmon et al. |
| 6,235,725 B1 | 5/2001 | Ahmed |
| 6,261,539 B1 | 7/2001 | Adjei et al. |
| 6,287,540 B1 | 9/2001 | Trofast |
| 6,303,145 B2 | 10/2001 | Jerussi et al. |
| 6,369,115 B1 | 4/2002 | Ward |
| 6,448,296 B2 | 9/2002 | Yasueda et al. |
| 6,461,591 B1 | 10/2002 | Keller et al. |
| 6,481,435 B2 | 11/2002 | Hochrainer et al. |
| 6,667,344 B2 | 12/2003 | Banerjee et al. |
| 6,814,953 B2 | 11/2004 | Banerjee et al. |
| 7,070,800 B2 | 7/2006 | Bechtold-Peters et al. |
| 7,348,362 B2 | 3/2008 | Banerjee et al. |
| 7,462,645 B2 | 12/2008 | Chaudry et al. |
| 7,473,710 B2 | 1/2009 | Chaudry et al. |
| 7,541,385 B2 | 6/2009 | Chaudry et al. |
| 8,114,912 B2 | 2/2012 | Chaudry et al. |
| 2001/0024641 A1 | 9/2001 | Yang |
| 2002/0032149 A1 | 3/2002 | Kensey |
| 2002/0061835 A1 | 5/2002 | Kensey |
| 2002/0081266 A1 | 6/2002 | Woolfe et al. |
| 2002/0099013 A1 | 7/2002 | Piccariello et al. |
| 2002/0103260 A1 | 8/2002 | Clarke et al. |
| 2002/0151597 A1 | 10/2002 | Banerjee et al. |
| 2002/0151598 A1 | 10/2002 | Banerjee et al. |
| 2002/0183293 A1 | 12/2002 | Banerjee et al. |
| 2003/0055026 A1 | 3/2003 | Banerjee et al. |
| 2003/0109510 A1 | 6/2003 | Gavin |

FOREIGN PATENT DOCUMENTS

| | | |
|---|---|---|
| DE | 19835346 A1 | 2/2000 |
| DE | 19847970 A1 | 4/2000 |
| EP | 0370632 A1 | 5/1990 |
| EP | 0616525 B1 | 9/1995 |
| EP | 1157689 A1 | 11/2001 |
| EP | 1229034 A1 | 8/2002 |
| EP | 1236467 A1 | 9/2002 |
| WO | 93/11773 A1 | 6/1993 |
| WO | 95/05805 A1 | 3/1995 |
| WO | 95/31964 A1 | 11/1995 |
| WO | 96/18384 A1 | 6/1996 |
| WO | 96/19198 A1 | 6/1996 |
| WO | 96/19968 A1 | 7/1996 |
| WO | 96/32095 A1 | 10/1996 |
| WO | 97/47286 A1 | 12/1997 |
| WO | 98/05302 A1 | 2/1998 |
| WO | 98/15280 A1 | 4/1998 |
| WO | 98/31351 A1 | 7/1998 |
| WO | 98/31352 A1 | 7/1998 |
| WO | 98/34595 A1 | 8/1998 |
| WO | 98/34596 A2 | 8/1998 |
| WO | 98/41193 A1 | 9/1998 |
| WO | 99/00134 A1 | 1/1999 |
| WO | 99/15182 A1 | 4/1999 |
| WO | 99/17754 A1 | 4/1999 |
| WO | 99/25359 A1 | 5/1999 |
| WO | 99/30703 A1 | 6/1999 |
| WO | 99/36095 A1 | 7/1999 |
| WO | 99/40939 A1 | 8/1999 |
| WO | 99/48476 A1 | 9/1999 |
| WO | 99/61003 A1 | 12/1999 |
| WO | 99/65464 A1 | 12/1999 |
| WO | 00/00181 A1 | 1/2000 |
| WO | WO00/00181 * | 1/2000 |
| WO | 00/06121 A1 | 2/2000 |
| WO | 00/07567 A1 | 2/2000 |
| WO | 00/16814 A1 | 3/2000 |
| WO | 00/23037 A1 | 4/2000 |
| WO | 00/23065 A2 | 4/2000 |
| WO | 00/28979 A1 | 5/2000 |
| WO | 00/30612 A1 | 6/2000 |
| WO | 00/30613 A1 | 6/2000 |
| WO | 00/33892 A1 | 6/2000 |
| WO | 00/47200 A1 | 8/2000 |
| WO | 00/48587 A1 | 8/2000 |
| WO | 00/51591 A1 | 9/2000 |
| WO | 00/53187 A1 | 9/2000 |
| WO | 00/53188 A1 | 9/2000 |
| WO | 01/22956 A2 | 4/2001 |
| WO | 01/27107 A2 | 4/2001 |
| WO | 01/32163 A1 | 5/2001 |
| WO | 01/39745 A2 | 6/2001 |
| WO | 01/54664 A1 | 8/2001 |
| WO | 01/70198 A1 | 9/2001 |
| WO | 01/78735 A1 | 10/2001 |
| WO | 01/78737 A1 | 10/2001 |
| WO | 01/78745 A1 | 10/2001 |
| WO | 01/85137 A2 | 11/2001 |
| WO | 01/89491 A1 | 11/2001 |
| WO | 01/89492 A1 | 11/2001 |
| WO | 02/03958 A1 | 1/2002 |
| WO | 02/07672 A2 | 1/2002 |
| WO | 02/11803 A1 | 2/2002 |
| WO | 02/28368 A1 | 4/2002 |
| WO | 02/30394 A2 | 4/2002 |
| WO | 02/34237 A1 | 5/2002 |
| WO | 02/38107 A2 | 5/2002 |
| WO | 02/43806 A2 | 6/2002 |
| WO | 02/45682 A1 | 6/2002 |
| WO | 02/49616 A1 | 6/2002 |
| WO | 02/051483 A1 | 7/2002 |
| WO | 02/060532 A1 | 8/2002 |
| WO | 02/060533 A2 | 8/2002 |
| WO | 02/060875 A1 | 8/2002 |
| WO | 02/060896 A1 | 8/2002 |
| WO | 02/060898 A1 | 8/2002 |
| WO | 02/062317 A2 | 8/2002 |
| WO | 02/083079 A2 | 10/2002 |
| WO | 02/083113 A2 | 10/2002 |
| WO | 03/024433 A2 | 3/2003 |
| WO | 03/047578 A1 | 6/2003 |

OTHER PUBLICATIONS

Remington, "Chapter 38: Stability of Pharmaceutical Products", The Science and Practice of Pharmacology, 1995, p. 639, 19th Edition.

Rosenborg et al., "Mass Balance and Metabolism of [(3)H]Formoterol in Healthy Men after Combined i.v. and Oral Administration-Mimicking Inhalation", Drug Metabolism and Disposition, 1999, pp. 1104-1116, 27(10).

Puigbo et al., "A New Therapeutical Alternative in the Management of Acute Asthma (Preliminary Report)", Alergia, Asma e Inmunologia, 2000, pp. 73-76, 11(2).

Maesen et al., "Formoterol Suspension Aerosol Comparison with Formoterol Solution Aerosol for 12 Weeks in Asthmatic Patients", Chest, 1992, pp. 1544-1549, 102.

Remington's Pharmaceutical Sciences, Seventeeth Edition, 1985, pp. 1455-1472.

West, Solid state chemistry and its application, Wilsy, New York, 1988, pp. 358, 365.

Vippagunta et al., "Crystalline solid," Advanced Drug Delivery, 2001, vol. 48, pp. 3-26.

Ulrich "Crystallization," Chapter 4, Kirk-Othmer Encyclopedia of Chemical techology, John, Wiley and Sons, 2002.

Bartow and Broagden"An update of its Pharmaceutical properties and therapeutic efficacy in management of asthma," Drugs, 1998, vol. 55, No. 2, pp. 303-322.

U.S. Appl. No. 13/052,792: Non-Final Office Action dated Feb. 28, 2013. Please note that this serial number is associated with the parent application of this present application.

(56) References Cited

OTHER PUBLICATIONS

Bedi "Inhaled Corticosteroids in COPD" Indian J Chest Allied Sci 2005, 47: 243-244.
Nials, A.T. et al., "Effects of beta-adrenoceptor agonists in human bronchial smooth muscle," Br. J. Pharmacol., 1993 110: 112-1116.
Nials, A.T, et al., "Formoterol on airway smooth muscle and human lung mast cells . . . ", European Journal of Pharmacology, 1994, 251: 127-135.
Mohammed, S.P. et al., "Duration of action of inhaled vs. Intravenous Beta2-adrenoceptor . . . ", Pulmonary Pharmacology & Therapeutics, 2000, 13: 287-292.
Barnes, "Scientific rationale for inhaled combination therapy with long-acting b2-agonists and corticosteroids," Eur. Respir. J. 19: 182-191 (2002).
Becker et al., "Formoterol, a new long-acting selective b2-adrenergic receptor agonist: Double-blind comparison with salbutamol and placebo in children with asthma" J. Allergy Clin. Immunol. 84: 891-895 (1989).
Campbell et al., "A comparison of the efficacy of long-acting B2-agonists: efornioterol via Turbohaler(R) and salrneterol via pressurized metered dose inhaler or Accuhaler(R), in mild to moderate asthmatics," Respiratory Medicine 93: 236-244 (1999).
Campestrini et al., "Automated and sensitive method for the determination of formoterol in human plasma by high-performance liquid chromatography and electrochemical detection," Journal of Chromatography B 704: 221-229 (1997).
Cazzola et al., "Long-Acting b2-Agonists in the Treatment of Acute Exacerbations of COPD," Clin. Drug Invest., 22(6): 168-174 (2002).
Daughjerg et al., "Duration of action of formoterol and salbutamol dry-powder inhalation in prevention of exercise-induced asthma in children," Acta Paediatr., 85: 684-687 (1996).
Dellamary et al., "Hollow Porous Particles in Metered Dose Inhalers," Pharmaceutical Research, 17(2): 168-174 (2000).
Derwent #000971705, WPI Acc. No. 1973-48969U/197335 citing German Patent Application No. DE 2305092 A, "Alpha-aminomethylbenzyl alcohol derives—prepd. by redn. of corresponding protected derives."
Derwent #010743444, WPI Acc. No. 1996-240399/199625 for German Patent Application DE 19541689, "Medicament contg. ciclesonid and beta2-sympathomimetic for treating chronic obstructive respiratory disease."
Derwent #012030009, WPI Acc. No. 1998-446919-199838 for PCT Patent Application WO 98/34595, "Pressurised liquid aerosol propellant for pharmaceutical inhalers—contains carbondioxide and hydro-fluoroalkane; give more consistent dosing and a better particle size spectrum."
Derwent #013011 051, WPI Acc. No. 2000-1829031200016 for PCT Patent Application WO 00/06121, "Aerosol propellant comprising dinitrogen monoxide and hydrofluoroalkane and optionally containing a pharmaceutically active substance."
Derwent #013023586, WPI Acc. No. 2000-195437/200017 for PCT Patent Application WO 00/07567, "Aerosol formulation of drug administration, containing small amount of cromoglycate or nedocromil salt as drug carrier to improve dispersion stability and accuracy of dosing."
Derwent #013024375, WPI Acc. No. 2000-196226/200018 for German Patent Application DE19835346, "Two-part drug capsule for use in powder inhalers is formed from hydrophobic plastics, preferably high density polyethylene."
Derwent #013132855, WPI Acc. No. 2000-304726/200027 for German Patent DE 19847970, "Stable concentrated liquid formulation of inhalable drug, e.g., formoterol or salbutamol, in solution or suspensionmedium, used after dilution for treatment of respiratory disorders by inhalation."
Derwent #013227765, WPI Acc. No. 2000-399639/200034 for PCT Patent Application WO 00/28979, "Use of magnesium state for stabilization of dry powder inhalation formations to improve resistance to moisture."

Derwent #013790372, WPI Acc. No. 2001-274583/200129 for PCT Patent Application WO 01/22956, "Drug combination of soft steroid and beta-2-adrenoreceptor agonist, administered by inhalation for effective treatment of respiratory of allergic diseases, e.g, asthma.".
Derwent #014808338, WPI Acc. No. 2002-629044/200268 for PCT Patent Application WO 02/060533, "Medicament containing a betamimetic and an oxitropium salt useful for the treatment of respiratory disorders with reduced side effects."
Derwent #014816787, WPI Acc. No. 2002-637493/200269 for PCT Patent Application WO 02/060532, "Medicament containing a betamimetic and an ipratropium salt useful for the treatment of respiratory disorders with reduced side effects."
Eidkelberg et al., "Ligand-independent Activation of the Glucocorticoid Receptor by b2-Adrenergic Receptor Agonists in Primary Human Lung Fibroblasts and Bascular Smooth Muscle Cells," J. Biol. Chem. 272(2): 1005-1010 (1999).
Ekstrom et al., "Low-dose formoterol Turbuhaler(R) (Oxis(R)) b.i.d., a 3-month placebo-controlled comparison with terbutaline (q.i.d.)," Respiratory Medicine 92: 1040-1045 (1998).
Flovent, Glaxo Wellcome Inc., Physicians' Desk Reference, 54th Ed., (2000). pp. 1186-1189.
Farmer et al., "b-Adrenergic agonists exert their "anti-inflammatory" effects in monocytic cells through the IkB/NF-kB pathway," Am. J. Physiol. Lung. Cell. Mol. Physiol. 279: 1675-682 (2000).
Greening et al., "Added salmeterol versus higher-dose corticosteroid in asthma patients with symptoms on existing inhaled corticosteroid," The Lancet, 344: 219-244(1994).
Grootendorst et al., "Effect of oral prednisolone on the bronchoprotective effect of formoterol in patient with persistent asthma," Eur. Respir. J. 17: 374-379 (2001).
Hardman et al. (Eds.), Goodman Gilman's The Pharmacological Basis of Therapeutics, 1996, p. 665.
Ida "Comparison of the Action of BD 40A lind some Other b-Adrenoceptor Stimulants on the Isolated Trachea and Atria of the Guinea Pig" Arzneim.-Forsch. (Drug Res) 26: 839-842 (1976).
Ida "Cardiorespiratory Activities of 3-Formylamino-4-hydroxy-a-(N-I-methyl-2-p-methoxyphenethylaminomethyl) benzylalcohol-hemifumarate (BD 40A) and some other b-Adrenoceptor Stimulants in Conscious Guinea Pigs" Arznein-Forsch. (Drug Res.) 26: 1337-1340 (1976).
Ida, Hisashi, "Pharmacology of Formoterol, (aRS)-3-formamido-4-hydroxy-a-[[[(aRS)-p-methoxy-a-methylphenethyl]
amino]methyl]benzyl alcohol fumatate dehydrate (BD 40A)," Oyo Yakui 21(2); 201-210 (1981).
Ito et al., "Glucocorticoid Receptor Recruitment of Histone Deacetylase 2 Inhibits Interleukin-1b-Induced Histone H4 Acetylation on Lysines 8 and 12," Molecular and Cellular Biology 20(18): 6892-6903 (2000).
Ito el al., "p65-activated Histone Acetyltransferase Activity is Repressed by Glucocorticoids," J. Biol. Chern. 276(32): 30208-30215 (2001).
Kamimura et al., "Quantitative Determination of the b-adrenoceptor stimulant Formoterol in Urine by Gas Chromatograph Mass Sptectrometry" J. Chrom. 229: 337-345(1982).
Kaumann et al., "Direct Labelling of myocardial B1-adrenoreceptors; Comparison of Binding Affinity of 3H-(−)-bisoprolol with its blocking potency," Arch. Pharm. 331: 27-39 (1985).
Korn et al., "Effects of formoterol and budesonide on GM-CSF and IL-8 secretion by triggered human bronchial epithelial cells," Eur. Respir. J. 17: 1070-1077 (2001).
Lebecque et al., "Effet d'une dose unique de formoterol par voie daerosol-doseur chez l'enfant asthmatique" Rev. Mal. Resp. 11: 47-50 (1994).
Lecaillon et al., "Parrnacokinetics and tolerability of formoterol in healthy volunteers after a single high dose of Foradil dry powder inhalation via aerolizer (TM)," Eur. J. Clin. Pharm. 55: 131-139 (1999).
Leckie et al., "Novel Therapy of COPD," Expert Opin. Investig. Drugs 9(1): 3-23 (2000).
Lemoine et al., "Direct labeling of B2-adrenoreceptors; Comparison of binding potency of 3H-1C1 118,551 and blocking potency of 1C1 118,551," Arch. Pharm 331: 40-51 (1985).

(56) References Cited

OTHER PUBLICATIONS

Lipworth et al., "Effects of Treatment with Formoterol on Bronchoprotection against Methacholine," Am. J. Med. 104: 431-438 (1998).
Lofdahl e al., "Formoterol Fumarate, a new b2-adrenoceptor agonist" Allergy 44: 264-271 (1989).
Lotvall et al., "Similar broncodilation with Formoterol delivered by Aerolizer or Turbuhaler," Can. Respir J. 6(5): 412-416 (1999).
Maesen et al., "Formoterol Suspension Aerosol" Chest 102: 1544-1549 (1992).
Maesen et al., "The Effect of Maximal Doses of Formoterol and Salbutamol from a Metered Dose Inhaler on Pulse Rates, ECG, and Serum Potassium Concentrations" Chest 99: 1367-1373 (1991).
Maesen et al., "Formoterol as Dry Powder Inhalation" Chest 101: 1376-1381 (1992).
Malolepszy et al., "Safety of Formoterol Turbuhaler(TM) at cumulative dose of 90 mg in patients with acute bronchial obstruction," Eur. Respir. J. 18: 928-934 (2001).
Miller et al., "Chronic Effects of the Novel Glucocorticosteroid RPR 106541 Administered to Beagle Dogs by Inhalation" Toxic. Path. 28: 226-236 (2000).
Murase et al., "New b-Adrenoreceptor Stimulants. Studies on 3 Acylamino-4-hydroxy-a-(N-substituted aminomethyl) benzyl Alcohols," Chem. Pharm. Bull. 26: 1368-1377 (1977).
Nielsen et al., "Flow-dependent effect of formoterol dry powder inhaled from the Aerolizer(R)," Eur. Respir. J. 10: 2105-2109 (1997).
Nightingale et al., "Differential Effect of Formoterol on Adenosine Monophophate and Histamine Reactivity in Asthma," Am. J. Respir. Crit. Care Med. 159: 1786-1790 (1999).
Nogrady, T., (Editor), Medicinal Chemistry: A Biochemical Approach, Oxford University Press, New York, pp. 388-392 (1985).
O'Connor, "Combination Therapy," Pulm. Pharm. & Ther. 11: 379-399 (1998).
Oddera et al., "Salmeterol Enhances the Inhibitory Activity of Dexamethasone on Allergen-Induced Blood Mononuclear Cell Activation," Respiration 65: 199-204 (1998).
Package Insert for: Advair (TM) Discus http://fb.e-files.net/PackageInsert?Advair.htn (Accessed on Sep. 26, 2002) (Copyright, 1999 Glaxo Wellcome Inc.).
Palmqvist et al, "Inhaled dry-powder formoterol and almeterol in asthmatic patients: onset of action, duration of effect and potency," Eur. Respir J. 10: 2484-2489 (1997).
Palmqvist et al., "Onset of Bronchodilation of Budesonide/formoterol vs. Salmeterol/Fluticasone in Single Inhalers," Pulm. Pharm. & Ther. 14: 29-34 (2001).
Pang et al., "Regulation of TNF-a-induced cotaxin release from cultured human airway smooth muscle cells by b2-agonists and corticosteroids," FASEB J, 15: 261-269 (2001).
Pang et al., "Synergistic Inhibition by b2-Agonists and Corticosteroids on Tumor Necrosis Factor-a-Induced Interlenkin-8 Release from Cultured Human Airway Smooth-Muscle Cells," Am. J. Respir. Cell Mol. Bio. 23: 79-85 (2000).
Pauwels et al., "Effect of Inhaled Formoterol and Budesonide on Exacerbations of Asthma," The New England J. Med. 337(20): 1405-1411 (1997).
Physicians' Desk Reference: PDR, Oradell, J.J.: Medical Economics Co., pp. 535-537: 480-482, 2828-2829 (2000).
Rico-Mendez et al, "Formoterol en polvo seco, dos veces al dia versus salbutamol aerosol, cuatro veces al dia, en pacientes con asma estable," Revista Alergia Mexico XLVI(5):130-135 (1999).
Ringdal et al., "Onset and duration of action of single doses of formoterol inhaled via Turbuhaler(R)." Resp. Med. 92: 1017-1021 (1998).
Sasaki et al., "Desposition and metabolism of formoterol fumarate, a new bronchodilator in rats and dogs," Xenobiotic 12: 803-832 (1982).

Scheen Pharma Clinics le Medicament du Mois le formoterol (Oxis Turbohaler), Rev. Med. Liege 53: 11: 715-718 (1998).
Schreurs et al., "A dose-response study with formoterol Turbuhaler(R) as maintenance therapy in asthmatic patients," Eur. Respir. J. 9:1678-1683 (1996).
Seberova et al., "Oxis(R) (formoterol given by Turbuhaler(R)) showed as rapid onset of action as salbutamol given by a pMDI," Rasp. Med. 94: 607-611 (2000).
Selroos et al., "Delivery Devices for Inhaled Asthma Medication," Clin. Immunother. 6: 273-299 (1996).
Seldon et al., "Albuterol Does Not Antagonize the Inhibitory Effect of Dexamethasone on Monocyte Cytokine Release," Am. J. Respir. Crit. Care Med. 157: 803-809 (1998).
Silvestri et al., "Fluticasone and salmeterol donregulate in vitro fibroblast proliferation and JCAM-1 or H-CAM expression," Eur. Respir. J. 18: 139-145 (2001).
Skold et al., "Glucocorticoids Augment Fibroblast-Medicated Contration of Collagen Gels by Inhibition of Endogenous PGE Production," Proc. Assoc. Am. Phys. 111(3): 239-258 (1999).
Smaldone et al., "Budesonide Inhalation Suspension in Chemically Compatable with Other Nebulizing Formulations," Chest 119(4) Suppl: 98S (2000).
Sovijarvi et al., "Preventive Effects of Inhaled Formoterol and Salbutamol on Histamine-Induced Bronchoconstriction—A Placebo-Controlled Study" Respiration 59: 279-282 (1992).
Stevens et al., "Use of the Steroid Derivative RPR 106541 in Combination with Site-Directed Mutagenesis for Enhanced Cytochrome P-450 3A4 Structure/Function Analysis" J. Pharma. Exp. Ther. 290: 594-602 (1999).
Stewart et al., "Acute formoterol administration has no argogenic effect in nonasthmatic athletes," Medicine & Science in Sports & Exercise 34(2): 213-217 (2002).
Tomioka et al., "Anti-Allergic Activities of the b-Adrenoreceptor Stimulant Formoterol (BD-40A)," Arch. Int. Pharmacodyn. 250: 279-292 (1981).
Totterman et al., "Tolerability to high doses of formoterol and terbutaline via Turbulhaler(R) for 3 days in stable asthmatic patients," Eur. Respir. J. 12: 573-579 (1998).
Ullman et al., "Formoterol inhaled as dry powder or via pressurized metered-dose inhaler in a cumulative dose-response study," Allergy 51: 745-748 (1996).
Van den Berg et al., "Evaluation of different doses of formoterol from a newly developed powder inhalation device in asthmatic patients" Fundam. Clin. Pharmacol. 9: 593-603 (1995).
Vianna et al., "Bronchodilators and Corticosteroids in the Treatment of Asthma," Drugs of Today 34(3): 203-223 (1998).
Wallin et al., "Time course and duration of bronchodilation with formoterol dry powder in patients with stable asthma" Thorax 48: 611-614 (1993).
Warne, The discovery and clinical development of RPR 106541: an airway-selective steroid for the treatment of asthma; Emerging Drugs 5(2): 231-239 (2000).
Wilding et al., "Effect of long term treatment with Salmeterol on asthma control: a double blind, randomized crossover study," British Med. J. 314: 1441-1446 (1997).
Woolcock et al., "Comparison of Addition of Salmeterol to Inhaled Steroids with Doubling of the Dose of Inhaled Steroids," Am. J. Respir. Crit. Care Med. 153: 1481-1488 (1996).
Yokoi et al., "The Development of a Radioimmunoassay for Formoterol" Life Sciences, 33:1665-1672 (1983).
Yoshida et al., "Acute, Subacute and Chronic toxicity Studies of a Bronchodilator Formoterol Fumarate (BD 40)" Oyo Yakuri, 26(5): 811-29 (1983).
Derwent WPI Acc. No. 2000-304726 for PCT Patent Application WO 00/23037, "Stable concentrated liquid formulation of inhalable drug, e.g. formoterol or salbutamol, in solution or suspension medium, used after dilution for treatment of respiratory disorders by inhalation".

* cited by examiner

FORMOTEROL/STEROID BRONCHODILATING COMPOSITIONS AND METHODS OF USE THEREOF

RELATED APPLICATIONS

This is a continuation application of U.S. patent application Ser. No. 12/625,328, filed Nov. 24, 2009 (now U.S. Pat. No. 8,623,851), which is a continuation application of U.S. patent application Ser. No. 10/145,978, filed May 13, 2002 (abandoned), which is a divisional application of U.S. patent application Ser. No. 09/887,496, filed Jun. 22, 2001 (abandoned). Benefit of priority under 35 U.S.C. §119(e) is also claimed to U.S. Provisional Patent Application No. 60/284,607, filed Apr. 17, 2001. The disclosures of the above-referenced applications are incorporated herein by reference in their entirety.

FIELD OF THE INVENTION

Compositions and methods are provided relating to treatment, prevention, or amelioration of one or more symptoms of bronchoconstrictive disorders. In particular, the compositions and methods herein include formoterol, and/or a derivative thereof, and a steroid, and/or a derivative thereof. The compositions are propellant-free, sterile unit dose or multidose inhalation solutions intended for administration via nebulization.

BACKGROUND OF THE INVENTION

Bronchoconstrictive disorders affect millions worldwide. Such disorders include asthma (including bronchial asthma, allergic asthma and intrinsic asthma, e.g., late asthma and airway hyper-responsiveness), chronic bronchitis and other chronic obstructive pulmonary diseases. Compounds having $\beta_2$-adrenoreceptor agonist activity have been developed to treat these conditions. Such compounds include, but are not limited to, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)-methyl)-5-isoxazolemethanol); Isoproterenol (4-(1-hydroxy-2-((1-methyl-ethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-diemthylethyl)amino)methyl)benzenemethanol); Fenoterol (5-(1-hydroxy-2-((2-(4-hydroxyphenyl)-1-methylethyl)-amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexo-prenaline (4,4'-(1,6-hexanediyl)-bis(imino(1-hydroxy-2,1-ethanediyl)))bis-1,2-benzenediol); Isoetharine (4-(1-hydroxy-2-((1-methylethyl)amino)-butyl)-1,2-benzenediol); Isoprenaline (4-(1-hydroxy-2-((1-methylethyl)-amino)ethyl)-1,2-benzenediol); Metaproterenol (5-(1-hydroxy-2-((1-methyl-ethyl)amino)ethyl)-1,3-benzenediol); Picumeterol (4-amino-3,5-dichloro-α-(((6-(2-(2-pyridinyl)ethoxy)hexyl)amino)methyl)benzenemethanol); Pirbuterol ($\alpha^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)-carbostyril hydrochloride).

These compounds are typically formulated for inhalation therapy. Aqueous or liquid formulations are preferred over formulations of solids. Powdered formulations are more difficult to administer, particularly to the young and elderly who are most often the patients in need of such therapy. Compounds, such as formoterol, which has many desirable properties, are not adequately stable in aqueous solutions to be formulated as liquids. Hence there is a need for formulations of compounds, such as formoterol, in a form that can be conveniently administered.

Other prophylactic therapeutics for use in treatment of bronchoconstrictive disorders include steroidal anti-inflammatory agents such as beclomethasone dipropionate (BDP), beclomethasone monopropionate (BMP), flunisolide, triamcenolone acetonide, dexamethasone; tipredane, ciclesonid, mometasone, mometasone furoate (Asmanex® Twisthaler™, Shering-Plough Corporation, Kenilworth, N.J.), RPR 106541, fluticasone, fluticasone propionate and budesonide. These agents can be formulated for inhalation therapy.

Effective treatment of asthma and other bronchoconstrictive disorders often requires combination therapy. It is advantageous to administer combinations of bronchodilators and other agents, such as anti-steroidal agents. Since some the $\beta_2$-adrenoreceptor agonist compounds are not available as aqueous or liquid formulations, combinations thereof with other agents, are not available as aqueous or liquid formulations. Since aqueous or liquid formulations are preferred, there is need to develop liquid formulations. Therefore, it is an object herein to provide stable liquid formulations of $\beta_2$-adrenoreceptor agonist compounds. It is a further object herein to improve the stability of existing liquid formulations.

SUMMARY OF THE INVENTION

Compositions and methods for treatment, prevention, or amelioration of one or more symptoms of bronchoconstrictive disorders are provided. The compositions provided herein are stable solutions of a bronchodilating agent, and/or a derivative thereof, and a prophylactic therapeutic agent, including, but not limited to, a steroid and/or a derivative thereof. The compositions are formulated in a pharmacologically suitable fluid that contains water and that are stable during long term storage. The compositions are suitable for direct administration to a subject in need thereof. Pharmacologically suitable fluids include, but are not limited to, polar fluids, including protic fluids. In certain embodiments herein, the compositions are aqueous solutions.

Compositions provided herein possess an estimated shelf-life of greater than 1, 2 or 3 months usage time at 25° C. and greater than or equal to 1, 2 or 3 years storage time at 5° C. In certain of these embodiments, using Arrhenius kinetics, >80% or >85% or >90% or >95% estimated bronchodilating agent remains after such storage. These compositions are particularly useful for administration via nebulization. In certain embodiments herein, the subject is a mammal. In other embodiments, the subject is a human.

The compositions provided herein are formulated to remain stable over a relatively long period of time. For example, the compositions provided herein are stored between −15° C. and 25° C., or between 2° C. and 8° C. In one embodiment, the compositions are stored at 5° C.

Among the bronchodilating agents for use herein are Albuterol (α'-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)-methyl)-6,7-isoquinolinediol); Clenbuterol (4-amino-3,5-dichloro-α-(((1,1-diemthylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino) ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexane-diyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino) ethyl)-1,2-benzenediol); Meta-proterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy) hexyl)-amino)methyl)benzenemethanol); Pirbuterol (α$^6$-(((1,1-dimethylethyl)-amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((±)-α$^1$-(((1,1-dimethylethyl)amino)methyl)-4-hydroxy-1,3-benzenedimethanol); (R)-Salbutamol; Salmeterol ((±)-4-hydroxy-α$^1$-(((6-(4-phenylbutoxy)hexyl)-amino)methyl)-1, 3-benzenedimethanol); (R)- Salmeterol; Terbutaline (5-(2-((1,1-dimethylethyl)amino)-1-hydroxyethyl)-1,3-benzenediol); Tulobuterol (2-chloro-α-(((1,1-dimethylethyl) amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Of particular interest herein is formoterol, having the formula:

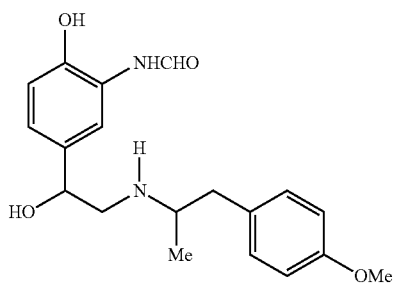

Formoterol for use in the compositions and methods provided herein includes 2-hydroxy-5-((1RS)-1-hydroxy-2-(((1RS)-2-(p-methoxy-phenyl)-1-methylethyl)amino)ethyl) formanilide; or a stereoisomer thereof; and also includes the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)-amino)ethyl)formanilide.

Prophylactic therapeutics for use in the compositions and methods herein include steroidal anti-inflammatory agents, including, but not limited to, beclomethasone dipropionate (BDP), beclomethasone monopropionate (BMP), flunisolide, triamcinolone acetonide, dexamethasone, tipredane, ciclesonid, rofleponide, mometasone, mometasone furoate (Asmanex® Twisthaler™, Sharing-Plough Corporation, Kenilworth, N.J.), RPR 106541, fluticasone or fluticasone propionate and budesonide, or derivatives thereof. In one embodiment, the steroidal anti-inflammatory is fluticasone, fluticasone propionate, budesonide, or a derivative thereof.

In certain embodiments, the compositions are administered via nebulization. Administration of a nebulized aerosol is preferred over the use of dry powders for inhalation in certain subject populations, including pediatric and geriatric groups.

In one embodiment, the compositions for use in the methods provided herein contain a pharmaceutically acceptable derivative of formoterol. In another embodiment, the compositions for use in the methods provided herein contain a pharmaceutically acceptable salt of formoterol. Pharmaceutically acceptable salts include, but are not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. In one embodiment, the compositions for use in the methods provided herein contain formoterol fumarate or formoterol fumarate dihydrate. In another embodiment, the compositions for use in the methods provided herein contain formoterol tartrate.

In another embodiment, the compositions for use in the methods provided herein contain budesonide or fluticasone propionate. Compositions containing formoterol, budesonide and a fluoroalkane propellant are disclosed in U.S. Pat. No. 6,004,537. Compositions containing formoterol and budesonide for dry powder inhalation or metered dose inhalation are disclosed in U.S. Pat. Nos. 5,674,860 and 5,972,919. These references do not disclose the compositions provided herein that are formulated in a pharmacologically suitable fluid, as defined herein, that contains water and that are stable during long term storage.

Also provided herein are combinations containing compositions provided herein. The compositions may be formulated separately or mixed in a single composition. The compositions contained in the combinations may be administered sequentially or intermittently. The compositions contained in the combinations can be mixed prior to use or can be formulated as a single composition. The combinations may further include a nebulizer. The combinations can be packaged as kits, which optionally contain other components, including instructions for use of the nebulizer and/or instructions for mixing the compositions if provided separately.

Any nebulizer is contemplated for use in the kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large, droplets from the mist by impaction and allows the droplets to return to the reservoir. The fine aerosol droplets thus produced are entrained into the lung by the inhaling air/oxygen.

Methods for the treatment, prevention, or amelioration of one or more symptoms of bronchoconstrictive disorders, including, but not limited to, asthma, including, but not limited to, bronchial asthma, allergic asthma and intrinsic asthma, e.g., late asthma and airway hyper-responsiveness; chronic bronchitis; and other chronic obstructive pulmonary diseases are provided. The methods involve administering an effective amount of a pharmaceutical composition provided herein to a subject in need of such treatment.

Articles of manufacture, containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction, are also provided.

DETAILED DESCRIPTION OF PREFERRED EMBODIMENTS

Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, formoterol refers to 2-hydroxy-5-((1RS)-1-hydroxy-2-(((1RS)-2-(p-methoxyphenyl)-1-methylethyl)amino)ethyl)formanilide; or a stereoisomer thereof. The term formoterol also refers to the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide.

As used herein, formoterol fumarate refers to a salt of formoterol having the formula (formoterol) *½ fumarate. Formoterol fumarate dihydrate refers to the dihydrate of formoterol fumarate.

As used herein, formoterol free base refers to the neutral, anhydrous form of formoterol. Thus, a recitation that a composition contains, e.g., 59 μg/mL of formoterol free base means that the composition contains 59 μg/mL of neutral, anhydrous formoterol. Such compositions may be prepared using a derivative of formoterol.

As used herein, budesonide refers to (RS)-11β,16α,17,21-tetrahydroxypregna-1,4-diene-3,20-dione cyclic 16,17-acetal with butraldehyde. The term budesonide refers to the (R) isomer, the (S) isomer, and mixtures thereof.

As used herein, fluticasone refers to (6α,9α,11β,16α,17α)-6,9-difluoro-11-hydroxy-16-methyl-3-oxo-17-hydroxyandrosta-1,4-diene-17-carbothioic acid, S-fluoromethyl ester. Fluticasone propionate refers to (6α, 9α, 11β, 16α,17α)-6,9-difluoro-11-hydroxy-16-methyl-3-oxo-17-(1-oxo-propoxy)androsta-1,4-diene-17-carbothioic acid, S-fluoromethyl ester.

As used herein, an aerosol is liquid or particulate matter dispersed in air. Aerosols include dispersions of liquids, including aqueous and other solutions, and solids, including powders, in air.

As used herein, a nebulized solution refers to a solution that is dispersed in air to form an aerosol. Thus, a nebulized solution is a particular form of an aerosol.

As used herein, a nebulizer is an instrument that is capable of generating very fine liquid droplet for inhalation into the lung. Within this instrument, the nebulizing liquid or solution is atomized into a mist of droplets with a broad size distribution by methods known to those of skill in the art, including, but not limited to, compressed air, ultrasonic waves, or a vibrating orifice. Nebulizers may further contain, e.g., a baffle which, along with the housing of the instrument, selectively removes large droplets from the mist by impaction. Thus, the mist inhaled into the lung contains fine aerosol droplets.

As used herein, a pharmacologically suitable fluid is a solvent suitable for pharmaceutical use which is not a liquified propellant gas. Exemplary pharmacologically suitable fluids include polar fluids, including protic fluids such as water.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, a mixture is a mutual incorporation of two or more substances, without chemical union, the physical characteristics of each of the components being retained.

As used herein, the stability of a composition provided herein refers to the length of time at a given temperature that greater than 80%, 85%, 90% or 95% of the initial amount of active ingredient, e.g., formoterol, is present in the composition. Thus, for example, a composition that is stable for 30 days at 25° C. would have greater than 80%, 85%, 90% or 95% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecule, preferably 1 to about 100, more preferably 1 to about 10, most preferably one to about 2, 3 or 4, solvent or water molecules. Formoterol salts and hydrates are used in certain embodiments herein.

As used herein, treatment means any manner in which one or more of the symptoms of a condition, disorder or disease are ameliorated or otherwise beneficially altered. Treatment also encompasses any pharmaceutical use of the compositions herein, such as use for treating cancer.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds for use in the compositions and methods provided herein may contain chiral centers. Such chiral centers may be of either the (R) or (S) configuration, or may be a mixture thereof. Thus, the compounds for use in the compositions provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

As used herein, bronchoconstriction refers to a reduction in the caliber of a bronchus or bronchi.

As used herein, undesired and/or uncontrolled bronchoconstriction refers to bronchoconstriction that results in or from a pathological symptom or condition. Pathological conditions include, but are not limited to, asthma and chronic obstructive pulmonary disease (COPD). Pathological symptoms include, but are not limited to, asthma and COPD.

As used herein, the statement that a composition is stable during "long term storage" means that the composition is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated bronchodilating agent remains after such storage.

A. Formoterol, Budesonide and Fluticasone Propionate

1. Formoterol

Formoterol (2-hydroxy-5-((1RS)-1-hydroxy-2-(((1RS)-2-(p-methoxy-phenyl)-1-methylethyl)amino)ethyl)formanilide) is derived from adrenaline and, as noted above, is used as a $\beta_2$-stimulator in inhalation therapy of respiratory diseases, particularly for the treatment of bronchial asthma. It has been reported that in patients with reversible obstructive respiratory diseases, formoterol has a bronchodilatory effect. This effect has a relatively rapid onset (approximately 1-3 minutes) and a relatively long duration (greater than 12 hours). Formoterol inhibits the release of leukotrienes and other messenger substances involved with inflammation, such as histamines. In addition, formoterol may bring about a hyperglycaemic activity.

To date, formoterol has been formulated as a dry powder and administered via devices such as the Turbuhaler® and the Aerolizer®. See, e.g., Seberova et al. (2000) *Respir. Med.* 94(6):607-611; Lotvall et al. (1999) *Can. Respir. J.* 6(5):412-416; Campbell et al. (1999) *Respir. Med.* 93(4):236-244; Nightingale et al. (1999) *Am. J. Respir. Crit. Care Med.* 159(6):1786-1790; Lecaillon et al. (1999) *Eur. J. Clin. Pharmacol.* 55(2):131-138; Bartow et al. (1998) *Drugs* 55(2):303-322; Ekstrom et al. (1998) *Respir. Med.* 92(8):1040-1045; Ringdal et al. (1998) *Respir. Med.* 92(8):1017-1021; Totterman et al. (1998) *Eur. Respir. J.* 12(3):573-579; Palmqvist et al. (1997) *Eur. Respir. J.* 10(11):2484-2489; Nielsen (1997) *Eur. Respir. J.* 10(9):2105-2109; Ullman et al. (1996) *Allergy* 51(10):745-748; Selroos et al. (1996) *Clin. Immunother.* 6:273-299; and Schreurs et al. (1996) *Eur. Respir. J.* 9(8):1678-1683.

Formoterol is also available as a tablet and a dry syrup in certain areas of the world (e.g., Atock®, marcketed by Yamanouchi Pharmaceutical Co. Ltd., Japan). Formoterol formulations are also available in other areas (e.g., Europe and U.S.) for propellant-based metered dose inhalers and dry powder inhalers (e.g., Turbuhaler®, Aerolizer® and Foradil Aerolizer®). None of these formulations are water based. Sterile, stable, aqueous based inhalation solutions of formoterol for nebulization are not available, nor have they been reported.

Compositions containing formoterol in combination with other active ingredients have been disclosed. See, e.g., U.S. Pat. Nos. 5,668,110, 5,683,983, 5,677,280 and 5,654,276 (formoterol and IL-5 inhibitors), U.S. Pat. No. 6,136,603 (formoterol and antisense modulators of IL-5), U.S. Pat. No. 5,602,110 (formoterol and milrinone), U.S. Pat. No. 5,525,623 (formoterol and a tryptase inhibitor), U.S. Pat. Nos. 5,691,336, 5,877,191, 5,929,094, 5,750,549 and 5,780,467 (formoterol and a tachykinin receptor antagonist); and International Patent Application Publication Nos. WO 99/00134 (formoterol and rofleponide) and WO 99/36095 (formoterol and a dopamine $D_2$ receptor agonist).

Other compositions containing formoterol have been disclosed in U.S. Pat. Nos. 5,677,809, 6,126,919, 5,733,526, 6,071,971, 6,068,833, 5,795,564, 6,040,344, 6,041,777, 5,874,481, 5,965,622 and 6,161,536.

U.S. Pat. No. 6,150,418 discloses a "liquid active substance concentrate" containing formoterol in the form of its free base or in the form of one of the pharmacologically acceptable salts or addition products (adducts) thereof as active substance. This "liquid active substance concentrate" is reported to be a concentrated (i.e., greater than 10 mg/mL, preferably 75 to 500 mg/mL) solution or suspension that is stable for a period of several months possibly up to several years without any deterioration in the pharmaceutical quality. This patent teaches that it is the high concentration that allows for the stability of the concentrate. The "liquid active substance concentrate" is not suitable for direct administration to a subject.

U.S. Pat. No. 6,040,344 discloses an aqueous aerosol formulation of formoterol tartrate for use in a nebulizer. This patent states that the formulation disclosed therein is not attractive for long term storage.

2. Budenoside and Fluticasone Propionate

Budesonide, (RS)-11β,16α,17,21-tetrahydroxypregna-1,4-diene-3,20-dione cyclic 16,17-acetal with butraldehyde, is an anti-inflammatory, synthetic corticosteroid. Fluticasone propionate, (6α,11β,16α,17α)-6,9,-difluoro-11-hydroxy-16-methyl-3-oxo-17-(1-oxopropoxy)androsta-1,4-diene-17-carbothioic acid, S-fluoromethyl ester, is a synthetic fluorinated corticosteroid, and is known for topical dermatologic use. Topical corticosteroids constitute a class of primarily synthetic steroids used as anti-inflammatory and antipruritic agents. The mechanism of the anti-inflammatory activity of topical steroids, in general, is unclear. However, corticosteroids are thought to act by the induction of phospholipase A2 inhibitory proteins (lipocortins). It is postulated that these proteins control the biosynthesis of prostaglandins and leukotrienes by inhibiting the release of arachidonic acid.

B. Compositions for Use in Treatment, Prevention, or Amelioration of One or More Symptoms of Bronchoconstrictive Disorders Pharmaceutical compositions containing a $\beta_2$-adrenoreceptor agonist and a steroid for administration via nebulization are provided. The compositions are sterile filtered and filled in vials, including unit dose vials providing sterile unit dose formulations which are used in a nebulizer and suitably nebulized. Each unit dose vial is sterile and is suitably nebulized without contaminating other vials or the next dose. The bulk sterile formulation is sterilized by steam, gamma radiation or is prepared using sterile steroidal powder.

The unit dose vials are formed in a form-fill-seal machine or by any other suitable method known to those of skill in the art. The vials may be made of plastic materials that are suitably used in these processes. For example, plastic materials for preparing the unit dose vials include, but are not limited to, low density polyethylene, high density polyethylene, polypropylene and polyesters. In one embodiment, the plastic material is low density polyethylene.

In one embodiment, the $\beta_2$-adrenoreceptor agonist in formoterol, or a pharmaceutically acceptable derivative thereof. In other embodiments, the formoterol for use in the compositions provided herein is formoterol fumarate. Formoterol refers to 2-hydroxy-5-((1RS)-1-hydroxy-2-(((1RS)-2-(p-methoxyphenyl)-1-methylethyl)amino)ethyl)formanilide; or a stereo-isomer thereof. The term formoterol also refers herein to the single enantiomers 2-hydroxy-5-((1S)-1-hydroxy-2-(((1S)-2-(p-methoxyphenyl)-1-methylethyl) amino)ethyl)formanilide and 2-hydroxy-5-((1R)-1-hydroxy-2-(((1R)-2-(p-methoxyphenyl)-1-methylethyl)amino)ethyl) formanilide.

In one embodiment, the compositions contain, in addition to a steroidal anti-inflammatory agent, including, but not limited to, budesonide and fluticasone propionate, formoterol free base at a concentration of about 5 µg/mL to about 2 mg/mL. In other embodiments, the maximum concentration of formoterol free base in the compositions is 1.5 mg/mL. In further embodiments, the concentration of formoterol free base in the compositions is about 10 µg/mL to about 1 mg/mL, or about 50 µg/mL to about 200 µg/mL. In other embodiments, the compositions contain formoterol fumarate at a concentration of about 80 µg/mL up to about 175 to 200 µg/mL. In further embodiments, the compositions contain formoterol fumarate at a concentration of about 90 µg/mL up to about 125 to 150 µg/mL. The formoterol fumarate is formulated, in certain compositions provided herein, at a concentration of about 100 µg/mL. The formoterol fumarate is formulated, in other compositions provided herein, at a concentration of about 85 µg/mL or about 170 µg/mL. In one embodiment, the formoterol fumarate is formulated for single dosage administration via nebulization at a concentration of about 100 µg/mL. In another embodiment, the compositions contain formoterol free base at a concentration of about 40 to about 150 µg/mL, particularly about 59 or about 118 µg/mL.

The compositions provided herein further contain, in addition to a $\beta_2$-adrenoreceptor agonist, including formoterol, a seroidal anti-inflammatory agent, including, but not limited to, budesonide or fluticasone propionate. Budesonide is (RS)-11β,16α,17,21-tetrahydroxypregna-1,4-diene-3,20-dione cyclic 16,17-acetal with butraldehyde. Budesonide also refers to the (R) isomer, the (S) isomer, and mixtures thereof. Fluticasone propionate refers to (6α,11β,16α,17α)-6,9-difluoro-11-hydroxy-16-methyl-3-oxo-17-(1-oxopropoxy)androsta-1,4-diene-17-carbothioic acid, S-fluoromethyl ester.

In one embodiment, the compositions contain budesonide or fluticasone propionate at a concentration of about 5 µg/mL to about 2 mg/mL In another embodiment, the compositions contain budesonide at a concentration of about 75 µg/mL to about 500 µg/mL, or about 125 µg/mL to about 500 µg/mL. In certain embodiments, the compositions contain budesonide at a concentration of about 125 µg/mL or 250 µg/mL. In another embodiment, the compositions contain fluticasone propionate at a concentration of about 75 µg/mL to about 1000 µg/mL, or about 250 µg/mL to about 1000 µg/mL. In further embodiments, the compositions contain fluticasone propionate at a concentration of about 125 µg/mL or about 250 µg/mL.

The compositions are formulated as solutions or suspensions with a pharmacologically suitable fluid. Pharmacologically suitable fluids include, but are not limited to, polar solvents, including, but not limited to, compounds that contain hydroxyl groups or other polar groups. Such solvents include, but are not limited to, water or alcohols, such as ethanol, isopropanol, and glycols including propylene glycol, polyethylene glycol, polypropylene glycol, glycol ether, glycerol and polyoxyethylene alcohols.

Polar solvents also include protic solvents, including, but not limited to, water, aqueous saline solutions with one or more pharmaceutically acceptable salt(s), alcohols, glycols or a mixture thereof. For a saline solution as the solvent or as a component thereof, particularly suitable salts are those which display no or only negligible pharmacological activity after administration.

In the embodiments herein, the compositions have a pH of about 2.0 to about 8.0. The particular pH of a given composition for long term storage provided herein may be determined empirically using standard stability assays well known to those of skill in the art (see, e.g., the Examples). For example, in certain embodiments, the compositions have a pH of about 4.0 to about 6.0, or about 4.5 to about 5.5. In certain of the above embodiments, the compositions are formulated at a pH of about 4, 4.4 or 4.6 up to about 5.5, 5.7 or 6. In other embodiments, the pH is about 5.0. It has been found herein that the rate constant for decomposition of an aqueous solution of formoterol is dependent on pH. The rate constant ($k_{obs}$) at 60° C. at a pH of 3, 4, 5 and 7 is approximately 0.62, 0.11, 0.044 and 0.55 day$^{-1}$, respectively. Therefore, the decomposition of formoterol in aqueous solution at 60° C. at a buffer concentration of 5 mM and an ionic strength of 0.05 is slowest at a pH of about 5.0.

The solubility of formoterol in aqueous solution has been found herein to be dependent on pH. Thus, at a pH of between about 5 and about 7, the aqueous solubility of formoterol at ambient temperature is approximately 2.2 mg/mL. At a pH of about 4, the aqueous solubility of formoterol at ambient temperature is approximately 3 mg/mL, while at a pH of about 3, the aqueous solubility of formoterol at ambient temperature is about 4.8 mg/mL. The solubility of formoterol in pure water, for example, high performance liquid chromatography (HPLC) water, at ambient temperature is approximately 2 mg/mL.

In other of the above embodiments, the compositions further contain a buffer, including, but not limited to, citric acid/phosphate, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)iminotris-(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxy-methyl)methyl-amino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxymethyl)methyl-amino)-2-hydroxypropanesulfonic acid), TRIZMA® (tris(hydroxymethyl-aminomethane), HEPPSO (N-(2-hydroxyethyl)piperazine-N'-(2-hydroxy-propanesulfonic acid), POPSO (piperazine-N,N-bis(2-hydroxypropane-sulfonic acid)), TEA (triethanolamine), EPPS(N-(2-hydroxyethyl)-piperazine-N'-(3-propanesulfonic acid), TRICINE (N-tris(hydroxymethyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl)methyl-3-amino-propanesulfonic acid), AMPD (2-amino-2-methyl-1,3-propanediol), and/or any other buffers known to those of skill in the art. In one embodiment, the buffer is citric acid/phosphate buffer, acetate buffer, citrate buffer or phosphate buffer. In another embodiment, the buffer is a citrate buffer (citric acid/sodium citrate). The buffer concentration has been found herein to affect the stability of the composition. Buffer concentrations for use herein include from about 0 or 0.01 mM to about 150 mM, or about 1 mM to about 20 mM. In one embodiment, the buffer concentration is about 5 mM. In another embodiment, the buffer concentration is about 1 mM to about 50 mM, or about 20 mM. The kinetic-pH profile of formoterol is dependent on buffer concentration. At low and approximately neutral conditions, increasing the buffer concentration from 5 mM to 20 mM increased the rated constant of decomposition significantly. However, no noticeable differences in rate constant were observed in the pH region of about 4.5 to about 5.5 with increasing buffer concentration from 5 mM to 20 mM. The particular buffer and buffer concentration of a given composition for long term storage provided herein may be determined empirically using standard stability assays well known to those of skill in the art (see, e.g., the Examples).

The ionic strength of the compositions provided herein also has been found herein to affect the stability of the composition. Ionic strengths of the compositions provided herein are from about 0 to about 0.4, or from about 0.05 to about 0.16. Compositions having a lower ionic strength exhibit improved stability over formulations having higher ionic strength. The rate constant of decomposition was essentially the same at ionic strength 0.05 to 0.1, but increased to some extent at ionic strength of 0.2. The particular ionic strength of a given composition for long term storage provided herein may be determined empirically using standard stability assays well known to those of skill in the art (see, e.g., the Examples).

In embodiments where the pharamacologically suitable fluid is a saline solution, tonicity adjusting agents may be added to provide the desired ionic strength. Tonicity adjusting agents for use herein include those which display no or only negligible pharmacological activity after administration. Both inorganic and organic tonicity adjusting agents may be used in the compositions provided herein. Tonicity adjusting agents include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, proplyene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In certain embodiments, the tonicity adjusting agent is sodium chloride, which is present at a concentration of from about 0 mg/mL to about 10, 15 or 20 mg/mL. In further embodiments, the compositions contain sodium chloride at a concentration of from about 0 mg/mL to about 7.5 mg/mL. In another embodiment, the compositions contain sodium chloride at a concentration of 0 mg/mL, 1.5 mg/mL, 6.8 mg/mL or 7.5 mg/mL. In these embodiments, the pharmacologically suitable fluid is aqueous saline.

The storage temperature of the compositions provided herein also has been found herein to affect the stability of the composition. Compositions stored at a lower temperature exhibit improved stability over formulations stored at higher temperatures. The effect of temperature on the rate constant of decomposition at pH 5, a buffer concentration of 5 mM, and an ionic strength of 0.05, was linear according to Arrhenius kinetics, i.e., when Ln $k_{obs}$ was plotted against 1/T, where T is the temperature in degree Kelvin.

The estimated shelf-life of formoterol in the compositions provided herein is significantly greater than that reported for known formoterol compositions. The estimated shelf-life of formoterol in the compositions provided herein is about 6.2 years at 5° C. and about 7.5 months at 25° C. The estimated formoterol concentrations in the compositions provided herein as a function of storage time at 5° C. and usage time at 25° C. was determined. It is estimated that greater than 90% of the initial formoterol present in the composition remains after 3 months of usage time at 25° C. and 3 years of storage time at 5° C. as well as after 0.5 months of usage time at 25° C. and 1 year of storage time at 5° C.

In certain embodiments, the compositions provided herein are prepared containing formoterol fumarate at a nominal concentration of 0.1 mg/mL at the indicated pH and citric acid/phosphate buffer concentrations. The solutions were stored at 60° C. In these compositions, formoterol is relatively more stable at a pH from about 4 to about 5, and is also more stable at lower buffer concentration.

The compositions provided herein also may include excipients and additives. The particular excipient or additive for use in the compositions for long term storage provided herein may be determined empirically using methods well known to those of skill in the art (see, e.g., the Examples). Excipients and additives are any pharmacologically suitable and therapeutically useful substance which is not an active substance. Excipients and additives generally have no pharmacological activity, or at least no undesirable pharmacological activity. The excipients and additives include, but are not limited to, surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. In another embodiment, particularly in the suspension formulations provided herein, the complexing agent is sodium edetate. In these embodiments, the compositions contain sodium edetate at a concentration of about 0.05 mg/mL to about 0.5 mg/mL, or about 0.1 mg/mL to about 0.2 mg/mL.

Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

In certain embodiments herein, particularly in the solution formulations provided herein, the compositions contain vitamin E TPGS 10 (d-α-tocopheryl polyethylene glycol 1000 succinate). In these embodiments, vitamin E TPGS is present at a concentration of about 0 mg/mL to about 100 mg/mL, or about 5 mg/mL to about 50 mg/mL. In certain embodiments herein, the compositions contain vitamin E TPGS at a concentration of 10 mg/mL, 20 mg/mL, 30 mg/mL or 50 mg/mL.

The compositions provided herein also may include a cosolvent, which increases the solubility of additives or the active ingredient(s). The particular cosolvent for use in the compositions for long term storage provided herein may be determined empirically using methods well known to those of skill in the art (see, e.g., the Examples). Cosolvents for use herein include, but are not limited to, hydroxylated solvents or other polar solvents, such as alcohols such as isopropyl alcohol, glycols such as propylene glycol, polyethylene glycol, polypropylene glycol, glycol ether, glycerol, and polyoxyethylene alcohols. In certain embodiments herein, particularly in the solution formulations provided herein, the compositions contain a glycol. In other embodiments, the compositions contain propylene glycol and/or polyethylene glycol, including polyethylene glycol 400. In these embodiments, the glycol is present at a concentration of about 0 mg/mL to about 100 mg/mL, or about 5 mg/mL to about 50 mg/mL. In further embodiments, the compositions contain propylene glycol at a concentration of 17 mg/mL or 20 mg/mL. In other embodiments, the compositions contain polyethylene glycol 400 at a concentration of 10 mg/mL, 20 mg/mL, 30 mg/mL or 50 mg/mL.

The compositions provided herein, particularly the suspension formulations provided herein, may also contain one or more emulsifiers. The particular emulsifier for use in the compositions for long term storage provided herein may be determined empirically using methods well known to those of skill in the art (see, e.g., the Examples). Emulsifiers for use herein include, but are not limited to, polyoxyetheylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2-lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

In certain embodiments herein, the emulsifier(s) is (are) a polyoxyetheylene sorbitan fatty ester or polysorbate, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; sorbitan monostearate; sorbitan tristearate; sorbitan monolaurate; sorbitan mono-oleate; or sorbitan monopalmitate. In further embodiments, the emulsifier(s) is (are) polysorbate 80, sorbitan monolaruate or polyoxyethylene (20) sorbitan nmonolaurate.

C. Preparation of Compounds for Use in the Compositions

The preparation of the compounds used in the compositions provided herein is described below. Any such compound or similar compound may be synthesized according to a method discussed in general below or by only minor modification of the methods by selecting appropriate starting materials.

Formoterol may be prepared according to the method disclosed in U.S. Pat. No. 3,994,974. Briefly, 4-benzyloxy-3-nitro-α-bromoacetophenone is reacted with N-benzyl-N-(1-methyl-2-p-methoxyphenylethyl)amine to form the α-aminoacetophenone. This compound was subjected to the following series of reactions: (i) reduction of the ketone with sodium borohydride; (ii) reduction of the nitro group with aqueous hydrochloric acid and iron powder; (iii) amine formylation with acetic anhydride and formic acid; and (iv) catalytic reduction over 10% palladium on carbon to afford formoterol free base. Crystallization of the ½ fumarate salt from ethanol provides (formoterol) ½ fumarate.

The individual enantiomers of formoterol, 2-hydroxy-5-((1S)-1-hydroxy-2-(((1S)-2-(p-methoxyphenyl)-1-methylethyl)amino)ethyl)-formanilide and 2-hydroxy-5-((1R)-1-hydroxy-2-(((1R)-2-(p-methoxy-phenyl)-1-methylethyl)amino)ethyl)formanilide, may be prepared by the method disclosed in U.S. Pat. No. 6,040,344. Briefly, reaction of optically pure 4-benzyloxy-3-formamidostyrene oxide with an optically pure 4-methoxy-α-methyl-N-(phenylmethyl) benzeneethanamine, followed by debenzylation, affords the desired enantiomer of formoterol. Debenzylation may be accomplished by reduction with hydrogen gas in the presence of a noble metal catalyst, such as palladium on carbon.

The required optically pure 4-benzyloxy-3-formamidostyrene oxide may be prepared from 4-benzyloxy-3-nitro-α-bromoacetophenone by (i) reduction with vorane in the presence of an optically pure aminoindanol, (ii) hydrogenation over platinum oxide catalyst, (iii) formylation with formic acid and acetic anhydride, and (iv) epoxide formation in the presence of potassium carbonate.

The required optically pure 4-methoxy-α-methyl-N-(phenylmethyl)-benzeneethanamine may be prepared from 4-methoxyphenylacetone by (i) reductive amination with benzylamine in the presence of hydrogen and a platinum catalyst, and (ii) crystallization of the desired optically pure amine from the resulting racemic mixture as its mandelic acid salt.

Budesonide may be synthesized by the procedure disclosed in U.S. Pat. No. 3,929,768. Briefly, reaction of triamcinolon with propionaldehyde and catalyic perchloric acid in dry dioxane at ambient temperature provides, following chromatography on hydroxy-propylated, cross-linked dextran gel, budesonide.

Fluticasone propionate may be synthesized by the procedure disclosed in U.S. Pat. No. 4,335,121. Briefly, the corresponding carbothioic acid is prepared from the carboxylic acid precursor by reaction with dimethylthiocarbamoyl chloride in the presence of triethylamine. Reaction with bromochloromethane and sodium hydrogen carbonate in dimethylacetamide affords the corresponding S-chloromethyl carbothioate. This compound is treated with sodium iodide in acetone to give the corresponding S-iodomethyl carbothioate. Fluoride substitution of the iodo group is accomplished by reaction with silver fluoride in acetonitrile to afford the desired compound.

D. Formulation of Pharmaceutical Compositions

The compositions provided herein are prepared by procedures well known to those of skill in the art. For example, a solution formulations may be prepared by the procedure of EXAMPLE 1. Briefly, polyethylene glycol 400 and/or propolyene glycol, and a preservative, such as vitamin E TPGS, are mixed at about 42° C. until a homogeneous solution forms. The temperature is lowered and the steroidal anti-inflammatory agent is added. In a second vessel, formoterol fumarate dihydrate and the remaining ingredients are dissolved in approximately 70% water. The two solutions are mixed and the resulting solution is diluted with water to the desired volume.

Suspension formulations are prepared by the procedure of EXAMPLE 2. Briefly, all ingredients other than the steroidal anti-inflammatory agent and formoterol fumarate dihydrate are dissolved in about 40% water with mixing. The steroidal anti-inflammatory agent, which is micronized, is dispersed in the above mixture with high speed homogenization. Formoterol fumarate dihydrate is dissolved in 50% water and added to the steroidal suspension with mixing until a uniform suspension forms.

E. Evaluation of the Activity of the Compositions

Standard physiological, pharmacological and biochemical procedures are available for testing the compositions provided herein to identify those that possess bronchdilatory activity.

In vitro and in vivo assays that may be used to evaluate bronchodilatory activity are well known to those of skill in the art. See also, e.g., U.S. Pat. Nos. 3,994,974, and 6,068, 833; German Patent No. 2,305,092; Kaumann et al. (1985) *Naunyn-Schmied Arch. Pharmacol.* 331:27-39; Lemoine et al. (1985) *Naunyn-Schmied Arch. Pharmacol.* 331:40-51; Tomioka et al. (1981) *Arch. Int. Pharmacodyn.* 250:279-292; Dellamary et al. (2000) *Pharm. Res.* 17(2):168-174; Rico-Mendez et al. (1999) *Rev. Alerg. Mex.* 46(5):130-135; Seberova et al. (2000) *Respir. Med.* 94(6):607-611; Lotvall et al. (1999) *Can. Respir. J.* 6(5):412-416; Campbell et al. (1999) *Respir. Med.* 93(4):236-244; Nightingale et al. (1999) *Am. J. Respir. Crit. Care Med.* 159(6):1786-1790; Lecaillon et al. (1999) *Eur. J. Clin. Pharmacol.* 55(2):131-138; Bartow et al. (1998) *Drugs* 55(2):303-322; Ekstrom et al. (1998) *Respir. Med.* 92(8):1040-1045; Ringdal et at (1998) *Respir. Med.* 92(8):1017-1021; Totterman et al. (1998) *Eur. Respir. J.* 12(3):573-579; Palmqvist et al. (1997) *Eur. Respir. J.* 10(11):2484-2489; Nielsen et al. (1997) *Eur. Respir. J.* 10(9):2105-2109; Ullman et al. (1996) *Allergy* 51(10:745-748; Selroos et al. (1996) *Clin. Immunother.* 6:273-299; and Schreurs et al. (1996) *Eur. Respir. J.* 9(8):1678-1683.

F. Methods of Treatment of Bronchoconstrictive Disorders

The compositions provided herein are used for treating, preventing, or ameliorating one or more symptoms of a bronchoconstrictive disorders in a subject. In one embodiment, the method includes administering to a subject an effective amount of a composition containing a $\beta_2$-adrenoreceptor agonist, including, but not limited to, formoterol, and a steroidal anti-inflammatory agent, including, but not limited to, budesonide and fluticasone propionate, whereby the disease or disorder is treated or prevented, or one or more symptoms are ameliorated. The subject treated is, in certain embodiments, a mammal. In certain of these embodiments, the mammal is a human.

In another embodiment, the method provided herein includes oral administration of a composition provided herein. In certain embodiments herein, the composition is directly administered to a subject in need of such treatment via nebulization without dilution or other modification of the composition prior to administration.

The methods for treatment, prevention, or amelioration of one or more symptoms of bronchoconstrictive disorders, in another embodiment, further include administering one or more of (a), (b) or (c) as follows: (a) a $\beta_2$-adrenoreceptor agonist; (b) a dopamine ($D_2$) receptor agonist; or (c) an anti-cholinergic agent; simultaneously with, prior to or subsequent to the composition provided herein.

$\beta_2$-Adrenoreceptor agonists for use in combination with the compositions provided herein include, but are not limited to, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)-methyl)-6,7-isoquinolinediol); Clenbuterol (4-amino-3,5-dichloro-α-(((1,1-diemthylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-α-(((2-(4-methoxyphenyl)-1-methyl-ethyl)amino)methyl)benzenemethanol); Hexoprenaline (4,4'-(1,6-hexanediyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino)ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy)hexyl)-amino)methyl)benzenemethanol); Pirbuterol ($\alpha^6$-(((1,1-dimethylethyl)-amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)-amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Dopamine ($D_2$) receptor agonists include, but are not limited to, Apomorphine ((r)-5,6,6a,7-tetrahydro-6-methyl-4H-dibenzo[de,g]quinoline-10,11-diol); Bromocriptine ((5'α)-2-bromo-12'-hydroxy-2'-(1-methylethyl)-5'-(2-methylpropyl)ergotaman-3',6',18-trione); Cabergoline ((8β)-N-(3-(dimethylamino)propyl)-N-((ethylamino)carbonyl)-6-(2-propenyl)ergoline-8-carboxamide); Lisuride (N'-((8α)-9,10-didehydro-6-methylergolin-8-yl)-N,N-diethylurea); Pergolide ((8β)-8-((methylthio)methyl)-6-propylergoline); Levodopa (3-hydroxy-L-tryrosine); Pramipexole ((s)-4,5,6,7-tetrahydro-$N^6$-propyl-2,6-benzothiazolediamine); Quinpirole hydrochlrodie (trans-(−)-4-aR-4,4a,5,6,7,8,8a,9-octahydro-5-propyl-1H-pyrazolo[3,4-g]quinoline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thiazolo[4,5-d]azepin-2-amine). Other dopamine $D_2$ receptor agonists for use herein are disclosed in International Patent Application Publication No. WO 99/36095.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide. In certain embodiments, the compositions contain an anticholinergic agent, such as ipratropium bromide or tiotropium bromide, at a concentration of about 5 µg/mL to about 5 mg/mL, or about 50 µg/mL to about 200 µg/mL. In other embodiments, the compositions for use in the methods herein contain an anticholinergic agent, including ipratropium bromide and tiotropium bromide, at a concentration of about 83 µg/mL or about 167 µg/mL.

Other active ingredients for use herein in combination therapy, include, but are not limited to, IL-5 inhibitors such as those disclosed in U.S. Pat. Nos. 5,668,110, 5,683,983, 5,677,280 and 5,654,276; antisense modulators of IL-5 such as those disclosed in U.S. Pat. No. 6,136,603; milrinone (1,6-dihydro-2-methyl-6-oxo-[3,4'-bipyridine]-5-carbonitrile); milrinone lactate; tryptase inhibitors such as those disclosed in U.S. Pat. No. 5,525,623; tachykinin receptor antagonists such as those disclosed in U.S. Pat. Nos. 5,691,336, 5,877,191, 5,929,094, 5,750,549 and 5,780,467; leukotriene receptor antagonists such as montelukast sodium (Singular®, R-(E)]-1-[[[1-[3-[2-(7-chloro-2-quinolinyl)ethenyl)phenyl)-3-[2-(1-hydroxy-1-methylethyl)phenyl]-propyl]thio]methyl]cyclopropaneacetic acid, monosodium salt), 5-lypoxygenase inhibitors such as zileuton (Zyflo®, Abbott Laboratories, Abbott Park, Ill.), and anti-IgE antibodies such as Xolair® (recombinant humanized anti-IgE monoclonal antibody (CGP 51901; IGE 025A; rhuMAb-E25), Genentech, Inc.).

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

G. Nebulizers

The compositions provided herein are intended for administration to a subject in need of such treatment via nebulization. Nebulizers that nebulize liquid formulations containing no propellant are suitable for use with the compositions provided herein. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Siemens, Aerogen, Omron, Bremed, AirSep, Luminscope, Medisana, Mountain Medical, Aerosol Medical Ltd. (Colchester, Essex, UK), AFP Medical (Rugby, Warwickshire, UK), Bard Ltd. (Sunderland, UK), Carri-Med. Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrasonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JETAir Disposable nebulizer), Omron CompAir Elite Compressor Nebulizer System (NE-C21 and Elite Air Reusable Nebulizer), Pari LC Plus or Pari LC Star nebulizer with Proneb Ultra compressor, Pulmo-aide, Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, AVA-NEB, Micro Mist, and PulmoMate. Exemplary ultrasonic nebulizers for use herein include MicroAir, UltraAir, CompAir, Pulmosonic, Scout, 5003 Ultrasonic Neb, 5110 Ultrasonic Neb, 5004 Desk Ultrasonic Nebulizer, Mystique Ultrasonic, Siemens Ultra Nebulizer 145, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, Aeroneb™ Partable Nebulizer System, Aerodose™ Inhaler, 5001 Electromagnetic Neb 5002, Rotary Piston Neb, Lumineb I Piston Nebulizer 5500, and AeroEclipse Breath Actuated Nebulizer.

H. Articles of Manufacture

The compositions provided herein may be packaged as articles of manufacture containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

In one embodiment herein, the compositions are packaged with a nebulizer for direct administration of the composition to a subject in need thereof.

The following examples are included for illustrative purposes only and are not intended to limit the scope of the invention.

Example 1

Preparation of Solution Formulations

Polyethylene glycol 400 and/or propylene glycol and vitamin E TPGS were mixed in a stainless steel container with heating at about 42° C. until a homogeneous liquid formed. While maintaining the liquid phase, the temperature was lowered and the steroid active ingredient, e.g., budesonide or fluticasone propionate, was added. The nixing was continued until all of the drug substance had dissolved. In another container all other ingredients, including formoterol fumarate dihydrate, were mixed with about 70% water until a clear solution formed. The two solutions were mixed together until a homogeneous clear solution formed. The volume was made up with water and the solution was mixed to give the desired composition.

Using the above procedure, the following solution compositions containing the indicated ingredients in the indicated amounts were prepared. For each steroidal anti-inflammatory agent, a low strength and a high strength formulation was prepared.

| Budesonide/Formoterol solution formulations | | |
|---|---|---|
| | Concentration | |
| Ingredient | Low strength | High strength |
| Formoterol fumarate dihydrate | 85 µg/mL | 170 µg/mL |
| Budesonide | 125 µg/mL | 250 µg/mL |
| Vitamin E TPGS | 10 mg/mL | 20 mg/mL |
| Either: | | |
| Propylene glycol or | 17 mg/mL | 20 mg/mL |
| Polyethylene glycol 400 | 10 mg/mL | 20 mg/mL |
| Citrate buffer | 5 mM | 5 mM |
| Sodium Chloride | 7.5 mg/mL | 6.8 mg/mL |
| Water | q.s. | q.s. |

| Fluticasone propionate/Formoterol solution formulations | | |
|---|---|---|
| | Concentration | |
| Ingredient | Low strength | High strength |
| Formoterol fumarate dihydrate | 85 µg/mL | 170 µg/mL |
| Fluticasone propionate | 125 µg/mL | 250 µg/mL |
| Vitamin E TPGS | 30 mg/mL | 50 mg/mL |
| Either: | | |
| Propylene glycol or | 17 mg/mL | 20 mg/mL |
| Polyethylene glycol 400 | 30 mg/mL | 50 mg/mL |
| Citrate buffer | 5 mM | 5 mM |
| Sodium Chloride | 1.5 mg/mL | 0 mg/mL |
| Water | q.s. | q.s. |

Example 2

Preparation of Suspension Formulations

All ingredients, with the exception of formoterol fumarate dihydrate and the steroidal anti-inflammatory agent, e.g., budesonide or fluticasone propionate, were dissolved in about 40% water in a container with mixing. The steroidal active ingredient was added and the mixture was dispersed with high speed homogenization. Formoterol fumarate dihydrate was dissolved in about 50% water with mixing and the resulting solution was added to the steroidal suspension with mixing until a uniform suspension formed.

Using the above procedure, the following suspension formulations containing the indicated ingredients in the indicated amounts were prepared.

Budesonide/Formoterol suspension formulations

| Ingredient | Concentration |
|---|---|
| Formoterol fumarate dihydrate | 5-2000 µg/mL or 50-200 µg/mL |
| Budesonide | 125-500 µg/mL |
| Disodium edetate | 0.1-0.2 mg/mL |
| Polysorbate 80 | 0.2-0.3 mg/mL |
| Sodium chloride | 5-10 mg/mL |
| Citrate buffer | 1-20 mM |
| Water | q.s. |

Fluticasone propionate/Formoterol suspension formulations

| Ingredient | Concentration |
|---|---|
| Formoterol fumarate dihydrate | 5-2000 µg/mL or 50-200 µg/mL |
| Fluticasone propionate micronized | 250-1000 µg/mL |
| Sorbitan monolaurate | 0.05-0.2 mg/mL |
| Polyoxyethylene 20 sorbitan monolaurate | 0.1-0.3 mg/mL |
| Sodium chloride | 5-10 mg/mL |
| Citrate buffer | 1-20 mM |
| Water | q.s. |

Since modifications will be apparent to those of skill in this art, it is intended that this invention be limited only by the scope of the appended claims.

The invention claimed is:

1. A method for treating or ameliorating one or more symptoms of a bronchoconstrictive disorder comprising: providing a pharmaceutical composition packaged for single dosage administration, the composition including (i) formoterol, or a pharmaceutically acceptable salt or hydrate thereof in solution; and (ii) a steroidal anti-inflammatory agent, or a pharmaceutically acceptable salt thereof in solution; in a pharmacologically suitable fluid comprising water that is propellant-free; the composition as formulated has an estimated shelf-life of greater than 1 month usage time at 25° C. and greater than or equal to 1 year storage time when stored at 5° C., whereby greater than 80% of the initial amount of formoterol in the compositions remains at such time; and the formoterol free base concentration is about 5 µg/mL to about 118 µg/mL, whereby the composition is formulated for direct administration to a subject in need thereof; and without dilution, directly administering an effective amount of the composition as provided to a subject in need of such treatment.

2. The method of claim 1, wherein greater than about 90% of the initial formoterol is present in the composition after 1 month usage time at 25° C. and 1 year storage time at 5° C.

3. The method of claim 1, wherein the composition further comprises a tonicity adjusting agent.

4. The method of claim 3, wherein the tonicity adjusting agent is ammonium carbonate, ammonium chloride, ammonium lactate, ammonium nitrate, ammonium phosphate, ammonium sulfate, ascorbic acid, bismuth sodium tartrate, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, urea, urethan, uridine or zinc sulfate.

5. The method of claim 1, wherein the pharmaceutically acceptable salt of formoterol is formoterol fumarate.

6. The method of claim 1, wherein the pharmacologically suitable fluid comprises a buffer.

7. The method of claim 6, wherein the buffer is citric acid/phosphate, acetate, barbital, cacodylate, citrate, collidine, formate, maleate, phosphate, succinate, veronal acetate, MES (2-(N-morpholino)ethanesulfonic acid), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BES (N,N-bis(2-hydroxyethyl)-2-aminoethanesulfonaic acid), MOPS (3-(N-morpholino)propanesulfonic acid), TES (N-tris(hydroxylmethyl)methyl-2-aminoethanesulfonic acid), HEPES (N-(2-hydroxyethyl)piperazine-N-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxylmethyl)methylamino)-2-hydroxypropanesulfonic acid), HEPPSO (N-(2-hydroxyethyl)piperazine-N'-(2-hydroxypropanesulfonic acid), POPSO (piperazine-N,N'-bis(2-hydroxypropanesulfonicacid)), EPPS(N-(2-hydroxyethyl)piperazine-N'-(3-propanesulfonic acid), TRICINE (N-tris(hydroxylmethyl)methylglycine) GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxy-methyl)methyl-3-aminopropanesulfonic acid), or AMPD (2-amino-2-methyl-1,3-propanediol) buffer.

8. The method of claim 7, wherein the buffer is citrate buffer.

9. The method of claim 8, wherein the buffer concentration is from about 0.01 mM to about 150 mM.

10. The method of claim 9, wherein the buffer concentration is from about 1 mM to about 20 mM.

11. The method of claim 10, wherein the buffer concentration is about 5 mM.

12. The method of claim 1, wherein the pH of the composition is about 4.0 to about 6.0.

13. The method of claim 12, wherein the pH of the composition is about 4.5 to about 5.5.

14. The method of claim 13, wherein the pH of the composition is about 5.0.

15. The method of claim 6, wherein the buffer is citrate buffer and the pH of the composition is about 5.0.

16. The method of claim 1, wherein the steroidal anti-inflammatory agent is beclomethasone dipropionate, beclomethasone monopropionate, flunisolide, triamcinolone acetonide, dexamethasone, tipredane, ciclesonid, rofleponide, mometasone, mometasone furoate, fluticasone, fluticasone propionate, budesonide, or a pharmaceutically acceptable salt thereof.

17. The method of claim 16, wherein the steroidal anti-inflammatory agent is budesonide, fluticasone propionate, or a pharmaceutically acceptable salt thereof.

18. The method of claim 1, wherein the steroidal anti-inflammatory agent is fluticasone propionate.

19. A method for the treatment or amelioration of one or more symptoms of bronchoconstrictive disorders, comprising: (i) providing a packaged pharmaceutical composition comprising formoterol, or a pharmaceutically acceptable salt or hydrate thereof in solution, the pharmaceutical composition being in a pharmacologically suitable fluid comprising water that is propellant-free, wherein: the composition has an estimated shelf-life of greater than 1 month usage time at 25° C. and greater than or equal to 1 year storage time when stored at 5° C. whereby greater than 90% of the initial amount of formoterol in the compositions remains at such time;

the formoterol free base concentration is about 5 µg/mL to about 118 µg/mL, whereby the composition is formulated at a concentration for direct administration to a human in need thereof; (ii) without dilution, directly administering an effective amount of the composition as provided to a human; and (ii) simultaneously with, prior to, or subsequent to administering the formoterol composition, administering an effective amount of a pharmaceutical composition comprising a steroidal anti-inflammatory agent, or a pharmaceutically acceptable salt thereof, in solution.

20. The method of claim 19, wherein the steroidal anti-inflammatory agent is beclomethasone dipropionate, beclomethasone monopropionate, flunisolide, triamcinolone acetonide, dexamethasone, tipredane, ciclesonid, rofleponide, mometasone, mometasone furoate, fluticasone or fluticasone propionate, or budesonide, or a pharmaceutically acceptable salt thereof.

* * * * *